United States Patent
Swift et al.

(10) Patent No.: US 6,903,181 B2
(45) Date of Patent: Jun. 7, 2005

(54) METHODS OF SYNTHESIS OF POLYSUCCINIMIDE, COPOLYMERS OF POLYSUCCINIMIDE AND DERIVATIVES THEREOF

(75) Inventors: Graham Swift, Chapel Hill, NC (US); George H. Redlich, East Norriton, PA (US)

(73) Assignee: Folia, Inc, Birmingham, AL (US)

( * ) Notice: Subject to any disclaimer, the term of this patent is extended or adjusted under 35 U.S.C. 154(b) by 62 days.

(21) Appl. No.: 10/698,411

(22) Filed: Nov. 3, 2003

(65) Prior Publication Data

US 2004/0102602 A1 May 27, 2004

Related U.S. Application Data

(63) Continuation-in-part of application No. 10/307,349, filed on Dec. 2, 2002, now Pat. No. 6,686,440, and a continuation-in-part of application No. 10/307,387, filed on Dec. 2, 2002, now Pat. No. 6,686,441, which is a continuation of application No. 09/776,897, filed on Feb. 6, 2001, now Pat. No. 6,495,658.

(51) Int. Cl.$^7$ .............................................. C08G 69/10
(52) U.S. Cl. ...................... 528/328; 424/400; 424/401; 525/419; 525/420; 528/315; 528/322
(58) Field of Search ................................. 424/400, 401; 525/419, 420; 528/315, 322, 328, 363

(56) References Cited

U.S. PATENT DOCUMENTS 6,365,706 B1 * 4/2002 Ma ............................ 528/363
2004/0006198 A1 * 1/2004 Sikes ......................... 528/322

* cited by examiner

*Primary Examiner*—Terressa Boykin
(74) *Attorney, Agent, or Firm*—Stamatios Mylonakis

(57) ABSTRACT

Disclosed are methods of synthesis of polysuccinimide, copolymers and derivatives thereof: also disclosed are methods of forming derivatives by ring-opening initiation reactions.

23 Claims, 2 Drawing Sheets

METHODS OF SYNTHESIS OF POLYSUCCINIMIDE, COPOLYMERS OF POLYSUCCINIMIDE AND DERIVATIVES THEREOF

This application is a Continuation-In-Part of application Ser. No. 10/307,349 now U.S. Pat. No. 6,686,440 and Ser. No. 10/307,387, now U.S. Pat. No. 6,686 441, both filed Dec. 2, 2002, which are a Continuation and Continuation-In-Part, respectively, of application Ser. No. 09/776,897, filed Feb. 6, 2001, now U.S. Pat. No. 6,495,658, issued Dec. 17, 2002, all three of which are incorporated herein by reference in their entirety.

BACKGROUND OF THE INVENTION

1. Field of the Invention

The present invention relates to a process for the preparation of polysuccinimide, and derivatives; the polysuccinimide is formed in a supercritical fluid (SCF), such as liquid $CO_2$ or supercritical $CO_2$ in an organic cosolvent, starting with L-aspartic acid, and the derivatives are formed by a ring-opening reaction.

2. Discussion of the Related Art

L-Aspartic acid has been produced commercially since the 1980's via immobilized enzyme methods. The aspartic acid so produced mainly has been used as a component of the synthetic sweetener, N-aspartyl phenylalanine methyl ester (ASPARTAME®).

In a typical production pathway, a solution of ammonium maleate is converted to fumarate via action of an immobilized enzyme, maleate isomerase, by continuous flow over an immobilized enzyme bed. Next, the solution of ammonium fumarate is treated with ammonia also by continuous flow of the solution over a bed of the immobilized enzyme, aspartase. A relatively concentrated solution of ammonium asparate is produced, which then is treated with an acid, for example nitric acid, to precipitate aspartic acid. After drying, the resultant product of the process is powdered or crystalline L-aspartic acid. Prior art that exemplifies this production pathway includes U.S. Pat. No. 4,560,653 to Sherwin and Blouin (1985), U.S. Pat. No. 5,541,090 to Sakano et al. (1996), and U.S. Pat. No. 5,741,681 to Kato et al. (1998).

In addition, non-enzymatic, chemical routes to D,L aspartic acid via treatment of maleic acid, fumaric acid, or their mixtures with ammonia at elevated temperature have been known for over 150 years (see Harada, K., *Polycondensation of thermal precursors of aspartic acid. Journal of Organic Chemistry* 24, 1662–1666 (1959); also, U.S. Pat. No. 5,872,285 to Mazo et al. (1999)). The above chemical routes of maleic acid and ammonia are less sterically controlled as well as less quantitative and the product is a D,L racemic mixture. Although the non-enzymatic routines are significantly less quantitative than the enzymatic syntheses of aspartic acid, possibilities of continuous processes and recycling of reactants and by-products via chemical routes are envisioned.

Polymerization and copolymerization of L-aspartic acid alone or with other comonomers is known. As reviewed in U.S. Pat. No. 5,981,691 to Sikes (1999), synthetic work with polyamino acids, beginning with the homopolymer of aspartic acid, dates to the mid 1800's and has continued to the present. Interest in polyaspartates and related molecules increased in the mid 1980's as awareness of the commercial potential of these molecules grew. Particular attention has been paid to biodegradable and environmentally compatible polyaspartates for commodity uses such as detergent additives and superabsorbent materials in disposable diapers, although numerous other uses have been contemplated, ranging from water-treatment additives for control of scale and corrosion to anti-tartar agents in toothpastes.

There have been some teachings of producing copolymers of succinimide and aspartic acid or aspartate via thermal polymerization of maleic acid plus ammonia or ammonia compounds. For example, U.S. Pat. No. 5,548,036 to Kroner et al. (1996) taught that polymerization at less than 140° C. resulted in aspartic acid residue-containing polysuccinimides. However, the reason that some aspartic acid residues persisted in the product polymers was that the temperatures of polymerization were too low to drive the reaction to completion, leading to inefficient processes.

JP 8277329 (1996) to Tomida exemplified the thermal polymerization of potassium asparate in the presence of 5 mole % and 30 mole % phosphoric acid. The purpose of the phosphoric acid was stated to serve as a catalyst so that molecules of higher molecular weight might be produced. However, the products of the reaction were of a lower molecular weight than were produced in the absence of the phosphoric acid, indicating that there was no catalytic effect. There was no mention of producing copolymers of aspartate and succinimide; rather, there was mention of producing only homopolymers of polyaspartate. In fact, addition of phosphoric acid in this fashion to form a slurry or intimate mixture with the powder of potassium aspartate, is actually counterproductive to formation of copolymers containing succinimide and aspartic acid residue units, or to formation of the condensation amide bonds of the polymers in general. That is, although the phosphoric acid may act to generate some fraction of residues as aspartic acid, it also results in the occurrence of substantial amounts of phosphate anion in the slurry of mixture. Upon drying to form the salt of the intimate mixture, such anions bind ionically with the positively charged amine groups of aspartic acid and aspartate residues, blocking them from the polymerization reaction, thus resulting in polymers of lower molecular weight in lower yield.

Earlier, U.S. Pat. No. 5,371,180 to Groth et al. (1994) had demonstrated production of copolymers of succinimide and aspartate by thermal treatment of maleic acid plus ammonium compounds in the presence of alkaline carbonates. The invention involved an alkaline, ring-opening environment of polymerization such that some of the polymeric succinimide residues would be converted to the ring-opened, aspartate form. For this reason, only alkaline carbonates were taught and there was no mention of cations functioning themselves in any way to prevent imide formation.

More recently, U.S. Pat. No. 5,936,121 to Gelosa et al. (1999) taught formation of oligomers (Mw<1000) of aspartate having chain-terminating residues of unsaturated dicarboxylic compounds such as maleic and acrylic acids. These aspartic-rich compounds were formed via thermal condensation of mixtures of sodium salts of maleic acid plus ammonium/sodium maleic salts that were dried from solutions of ammonium maleate to which NaOH had been added. They were producing compounds to sequester alkaline-earth metals. In addition, the compounds were shown to be nontoxic and biodegradable by virtue of their aspartic acid composition. Moreover, the compounds retained their biodegradability by virtue of their very low Mw, notwithstanding the presence of the chain-terminating residues, which when polymerized with themselves to sizes about the oligomeric size, resulted in non-degradable polymers.

A number of reports and patents in the area of polyaspartics (i.e., poly(aspartic acid) or polyaspartate), polysuccinimides, and their derivatives have appeared more recently. Notable among these, for example, there have been disclosures of novel superabsorbents (U.S. Pat. No. 5,955,549 to Chang and Swift, 1999; U.S. Pat. No. 6,027,804 to Chou et al., 2000), dye-leveling agents for textiles (U.S. Pat. No. 5,902,357 to Riegels et al., 1999), and solvent-free synthesis of sulfhydryl-containing corrosion and scale inhibitors (EP 0 980 883 to Oda, 2000). There also has been teaching of dye-transfer inhibitors prepared by nucleophilic addition of amino compounds to polysuccinimide suspended in water (U.S. Pat. No. 5,639,832 to Kroner et al., 1997), which reactions are inefficient due to the marked insolubility of polysuccinimide in water.

U.S. Pat. No. 5,981,691 to Sikes, et al purportedly introduced the concept of mixed amide-imide, water-soluble copolymers of aspartate and succinimide for a variety of uses. The concept therein was that a monocationic salt of aspartate when formed into a dry mixture with aspartic acid could be thermally polymerized to produce the water-soluble copoly(aspartate, succinimide). The theory was that the aspartic acid comonomer when polymerized led to succinimide residues in the product polymer and the monosodium aspartate comonomer led to aspartate residues in the product polymer. It was not recognized that merely providing the comonomers was not sufficient to obtain true copolymers and that certain other conditions were necessary to avoid obtaining primarily mixtures of polyaspartate and polysuccinimide copolymers. In U.S. Pat. No. 5,981,691, the comonomeric mixtures were formed from an aqueous slurry of aspartic acid, adjusted to specific values of pH, followed by drying. There was no teaching of use of solutions of ammonium aspartate or any other decomposable cation plus NaOH, or other forms of sodium or other cations, for generation of comonomeric compositions of aspartic acid and salts of aspartate. Thus, although some of the U.S. Pat. No. 5,981,691 examples obtain products containing some copolymer in mixture with other products, particularly homopolymers, as discussed in the Summary of the Invention below, the theory that true copolymers could be obtained merely by providing the comonomers in the manner taught in U.S. Pat. No. 5,981,691 was not fully realized.

Thus, to date, there have been no successful disclosures of water-soluble or wettable, mixed amide/imide polyamino acids such as copolymers of aspartate and succinimide, related imide-containing polyamino acids, polysuccinimide or derivatives thereof.

SUMMARY OF THE INVENTION

One aspect of the invention relates to polymerizing aspartic acid to polysuccinimide in a supercritical fluid (SCF), such as liquid $CO_2$ or supercritical $CO_2$ in combination with an organic cosolvent. In another aspect of the present invention aspartic acid is polymerized in a supercritical fluid to form copoly(succinimide, aspartarte). In yet another aspect of the present invention the polysuccinimide or the copoly(succinimide, aspartate) formed in the supercritical fluid is derivatized to produce derivatives of the polysuccinimide and of the copoly(succinimide, aspartate). In another aspect of the present invention, the polysuccinimide or the copoly(succinimide, aspartate) formed in a supercritical fluid are subsequently isolated and melt processed. Dewatering stage or concentration of monomers may be done by any suitable technique including wiping film evaporator, drum drying, evaporation in a screw reactor or inline concentrator, etc.

DESCRIPTION OF THE PREFERRED EMBODIMENTS

Figure 1:
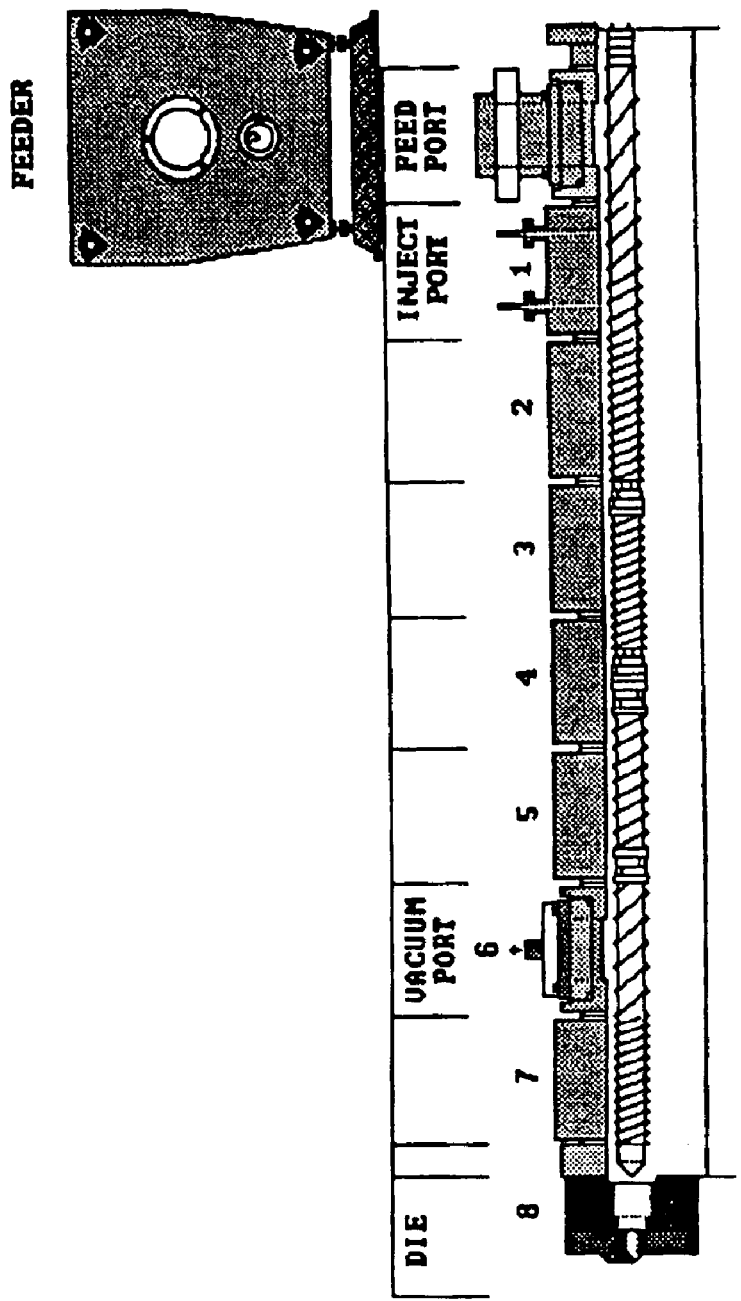
FIG. 1 depicts a diagram of a typical extrusion machine. The injection port allows the introduction of reactants into the injection machine for post reactions of the polymer or copolymers in the melt. The sections of the screw are separately heated and interchangeable. Thus, the injection port can be placed downstream in the injection machine depending on the required residence time required for a desired reaction.

These previous references fail to teach a method whereby a sufficiently intimate mixture of the comonomers is provided such that polymerization leads to a true copolymer with a significant number of both aspartate and succinimide residues or the synthesis of polysuccinimide.

A. Thermal Synthesis of Copoly(Succinimide-Aspartate)

A method has now been discovered providing a sufficiently intimate mixture of the comonomers and, therefore, allowing the production of a true copolymer with a significant number of both aspartate (also referred to as amide) residues or units and succinimide (also referred to as imide) units or residues, as schematically shown by the following reaction:

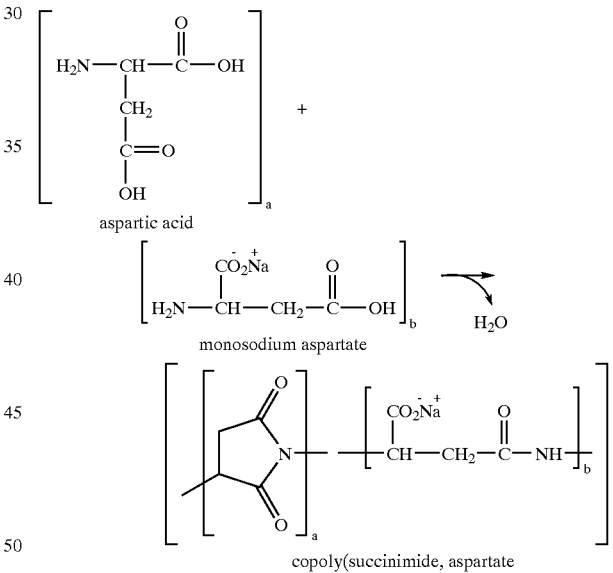

copoly(succinimide, aspartate)

The invention also can provide the resulting copolymers in isolated form. By isolated form it is meant that the copolymer is either: (a) in the substantial absence, e.g., less than 10%, preferably less than 5%, more particularly less than 1%, by weight of a polyaspartate or polysuccinimide homopolymer, (b) prepared by a method defined by this invention or (c) polyaspartate and/or polysuccinimide homopolymer from the copolymer.

Accordingly, the present invention teaches novel methods for producing mixed amide/imide copolymers of amino acids, as well as the resulting novel imide-containing polyamino acids themselves. Included are methods employing the monomers aspartic acid or aspartate salts having non-volatile or non-heat-decomposable cations. By aspartate or aspartate salt is meant a salt of the aspartate ion and any metallic cation, including alkali metal, alkaline earth metals or transition metals. Preferably the cations are alkali or alkaline earth metals, particularly Na, Mg, K, Ca, Rb, Sr, Cs and Ba, with sodium, magnesium, potassium and calcium, particularly sodium, being preferred. These monomers lead to amide formation. Other monomer, particularly aspartates having a volatile or heat-decomposable cation, preferably an ammonium or amine cation, lead to imide formation. In the following, the amide-generating cation will be represented by sodium ($Na^+$) and the imide-generating cation will be represented by ammonium ($NH_4^+$) but with the understanding that other cations creating the same effects for achieving the invention may be substituted. By volatile or heat-decomposable cation it is meant that the cation sufficiently dissociates from the aspartate anion under the given drying conditions such that the remaining aspartate unit can cyclize to a succinimide unit during the polymerization. Cations which have at least 50% dissociation in this manner under the given drying conditions are considered volatile or heat-decomposable and cations which do not dissociate at least 50% are considered non-volatile or non-heat decomposable.

In the present invention, some elements of the conventional, enzymatic processes for production of aspartic acid can be adapted for producing monomers useful in the invention. The production of the comonomer mixture, however, is a novel aspect. The method involves providing an intimate solution of an aspartate of a non-volatile cation and an aspartate of a volatile cation. By the term aspartate is meant an aspartic acid residue, either as a monomer or as a polymerized or copolymerized unit having its carboxyl group in ionic form associated with a cation, i.e., as —$COO^-$. Specifically, for example, an ammonium aspartate solution can be titrated with NaOH to a fractional molar equivalence of a sodium salt of aspartate and an ammonium salt of aspartate. This comonomeric solution is then dried to produce a comonomer mixture of a partial sodium salt of aspartic acid and free aspartic acid. By free aspartic acid is meant aspartic acid or a polymerized or copolymerized aspartic acid residue having its carboxyl group not in ionic form, i.e., —COOH. Because the dried comonomer mixture is prepared from the novel intimate solution of comonomers, an intimate dried mixture of these comonomers is obtained. Although not intending to be bound by this theory, it is believed that the mixture is intimate to the extent of exhibiting a salt lattice structure of the aspartate with the aspartic acid. It is possible for the dried comonomeric composition to also contain some residual ammonium aspartate, but in very small amounts, e.g., not exceeding 10% by weight, preferably not exceeding 5% by weight, more preferably not exceeding 2% by weight.

In effect, the aspartate of the volatile cation (e.g. ammonium) when dried from aqueous solution, is largely converted to powdered or crystalline aspartic acid. This is due to the loss of the decomposable cation, e.g., ammonia, as a vapor upon drying, with accompanying lowering of the pH of the evaporating solution as ammonia leaves the solution, for example, as a result of the following equilibrium being pulled to the left:

$\uparrow NH_3 \leftrightarrows NH_3 + H_2O \leftrightarrows NH_4OH \leftrightarrows NH_4^+ + OH^-$.

As is understood, however, by those skilled in the art, the term "dried" does not imply the complete absence of ammonia. Rather, the comonomer mixture might contain an amount of ammonia which is subsequently removed during the polymerization, as described below.

The sodium ion, on the other hand, has no significant vapor phase during drying and remains in the dried salt as a counter ion to aspartate monomers. Thus, the relative proportions of the comonomers, monosodium aspartate and aspartic acid, is set by the relative molar amounts of ammonium aspartate in solution and the NaOH added to the solution prior to drying.

The dried comonomer mixture is a clear, glassy solid at room temperature if drying occurs in vacuo or in an oxygen-depleted atmosphere. In the presence of atmospheric oxygen, the dried comonomer preparation has a pale yellow, glassy appearance.

The comonomer composition of the present invention may also be prepared via non-enzymatic, chemical production of solutions of ammonium aspartate. For example, maleic acid plus ammonia in water plus heating, preferably at an elevated pressure, may produce ammonium aspartate in solution. Typically, temperatures of 80 to 160° C., preferably 120 to 160° C. and a pressure of up to about 120 psi can be used, although other conditions may be useful depending on the particular circumstances. Upon addition of the desired amount of NaOH, this solution is dried to form the comonomer composition containing the mixture of the sodium aspartate salt and aspartic acid.

The comonomeric composition may also be obtained via coprecipitation from solution. For example, addition of a hydrophobe or downward adjustment of pH may lead to coprecipitation of the monomers. These may then be isolated, for example by filtration, for use in the production of the imide-containing polymers. Dewatering stage or concentration of monomers may be done by any suitable technique including wiping film evaporator, drum drying, evaporation in a screw reactor or inline concentrator, etc.

Also included are methods in which maleic acid plus ammonia plus soluble, non-alkali as well as alkali, cationic salts are used to internally generate a combination of aspartic acid and monosodium aspartate comonomers for thermal polymerization to produce water-soluble, imide containing copolymers.

In an additional embodiment the polysuccinimide of the present invention is derivatized in water in the presence of a combination of amines, such as ammonium hydroxide in combination with 2-aminoethanol. The resulting polysuccinimide derivative contains a free carboxylic acid and the amides of ammonia and aminoethanol. It is desirable in some uses to provide polysuccinimide in the absence of a sodium salt, usually formed in the hydrolysis of poly with sodium hydroxide. To avoid the presence of sodium salt, in a preferred embodiment of the present invention, the succinimide rings are hydrolyzed in the presence of a tertiary amine to form a tertiary amine salt of polyaspartic acid. Therefore by the proper combination of various amines, derivatives are made from polysuccinimide exhibiting higher molecular weight, in the order from 30,000 to 150,000 weight average including all increments in between, and reduced color. In an additional embodiment the polymerization is carried out in the presence of a catalyst, such as phosphoric and polyphosphoric acid, and any hydrogen acid.

B. Synthesis of Polysuccinimide (PSI) in a Supercritical Fluid

In another embodiment of the present invention a method has now been discovered allowing the production of polysuccinimide at high molecular weight and high yield in a supercritical fluid as a solvent. A supercritical fluid is a fluid medium that is at a temperature that is sufficiently high that it cannot be liquified by pressure. A supercritical fluid relates to dense gas solutions with enhanced solvation powers, and can include near supercritical fluids. The basis for a supercritical fluid is that at a critical temperature and pressure, the liquid and gas phases of a single substance can co-exist.

Further, supercritical fluids are unique states of matter existing above certain temperatures and pressures. As such, these fluids exhibit a high level of functionality and controllability that can influence not only the macrophysical properties of the fluid, but also influence nano-structures of molecules dissolved in them.

The supercritical fluid phenomenon is documented, for example, in the CRC Handbook of Chemistry and Physics, 67th Edition, pages F-62 to F-64 (1986–1987), published by the CRC Press, Inc., Boca Raton, Fla. At high pressures above the critical point, the resulting supercritical fluid, or "dense gas", attains densities approaching those of a liquid and assumes some of the properties of a liquid. These properties are dependent upon the fluid composition, temperature, and pressure. As used herein, the term "critical point" denotes the transition point at which the liquid and gaseous states of a substance merge with each other and represents the combination of the critical temperature and critical pressure for a given substance.

The compressibility of supercritical fluids is great just above the critical temperature where small changes in pressure result in large changes in the density of the supercritical fluid. The "liquid-like" behavior of a supercritical fluid at higher pressures results in greatly enhanced solubilizing capabilities compared to those of the "subcritical" compound, with higher diffusion coefficients and an extended useful temperature range compared to liquids. It has also been observed that as the pressure increases in a supercritical fluid, the solubility of the solute often increases by many orders of magnitude with only a small pressure increase.

Near-supercritical liquids also demonstrate solubility characteristics and other pertinent properties similar to those of supercritical fluids. Fluid "modifiers" can often alter supercritical fluid properties significantly, even in relatively low concentrations. In one embodiment, a fluid modifier is added to the supercritical fluid. These variations are considered to be within the concept of a supercritical fluid as used in the context of this invention. Therefore, as used herein, the phrase "supercritical fluid" also denotes a compound above, at, or slightly below the critical temperature and pressure (the critical point) of that compound.

The use of supercritical fluids in the production of polymers as a swelling, foaming or purification agent is known from various sources. Supercritical fluid serves to increase resin mobility thereby improving mixing and processing, to reduce the polymer glass transition temperature by swelling, and enabling processing at lower temperatures, and acts as a solvent for impurities (including unreacted monomer and residual conventional solvents) which may be removed during the processing to give high purity products. Moreover the fluid can be used to aerate the polymer by transition to non-critical gaseous state whereby a porous material may be obtained. Supercritical fluid has found application in incorporation of dyes and other inorganic materials which are insoluble in the supercritical fluid, for example inorganic carbonates and oxides, into polymers with a good dispersion to improve quality, in particular dispersion in products such as paints for spray coating and the like.

Accordingly, in another embodiment of the present invention an additive is dispersed into the polysuccinimide or copoly(succinimide-aspartate) or a derivative thereof formed in a supercritical fluid.

Examples of compounds which are known to have utility as supercritical fluids are, but are not limited to, $CO_2$, $NH_3$, $H_2O$, $N_2O$, xenon, krypton, methane, ethane, ethylene, propane, pentane, methanol, ethanol, isopropanol, isobutanol, $CClF_3$, $CFH_3$, cyclohexanol, $CS_2$, and a mixture thereof.

Due to the low cost, environmental acceptability, non-flammability, and low critical temperature of carbon dioxide, nitrous oxide, and water, supercritical carbon dioxide, nitrous oxide and/or $H_2O$ fluid is preferably employed in the present invention. More preferably carbon dioxide is employed in the present invention.

In another embodiment of the present invention, a cosolvent is preferably used in conjunction with the supercritical fluid as a polymerization vehicle. Suitable cosolvents include, but are not limited to, trans-2-hexenyl acetate, ethyl trans-3-hexenoate, methyl caproate, isobutyl isobutyrate, butyl acetate, butyl methacrylate, hexyl acetate, butyl butyrate, pentyl propionate, methyl ethanoate, ethyl caproate, methyl dodecanoate, 2-ethylbutyl acetate, methyl oleate, dodecyl acetate, methyl tridecanoate, soybean oil methyl esters, hexane, heptane, tetradecane, hexadecane, toluene, 1-hexadecene, 1-dodecanol, 1-nonanol, methyl alcohol, ethyl alcohol, n-propyl alcohol, isopropyl alcohol, allyl alcohol, n-butyl alcohol, isobutyl alcohol, sec-butyl alcohol, t-butyl alcohol, n-amyl alcohol, isoamyl alcohol, t-amyl alcohol, n-hexyl alcohol, cyclohexanol, n-octyl alcohol, octanol-2, n-decyl alcohol, lauryl alcohol, myristyl alcohol, cetyl alcohol, stearyl alcohol, benzyl alcohol and a mixture thereof.

The supercritical fluid is preferably maintained at a pressure from about 500 psi to about 2500 psi, more preferably from about 700 psi to about 2000 psi, and at a temperature from about 50° C. to about 300° C., more preferably from about 100° C. to about 250° C. The term "about" is used in the present application to denote a variation of 10% of the stated value.

The weight percentage of cosolvent and solute in the supercritical fluid is preferably from about 1% to about 20%, more preferably from about 5% to about 15%.

The weight average molecular weight of the polysuccinimide in accordance with the above process is in the order of from about 2,000 to about 10,000 Dalton, including all increments within that range, and preferably in the order of from about 3,000 to about 5,000 Daltons.

In another embodiment of the present invention the polymerization of aspartic acid to polysuccinimide in a supercritical fluid is carried out in the presence of a catalyst, preferably an acidic catalyst, such as phosphoric acid.

In another embodiment of the present invention, the polymerization is carried out in the presence of a thermal stabilizer or an antioxidant or a mixture thereof.

In an additional embodiment of the present invention, the polymerization of aspartic acid is performed in the dispersed phase. The term "dispersed phase" is herein used to denote a heterogeneous mixture where the monomer particles are suspended in the polymerization medium, where the polymerization medium forms the continuous phase.

In accordance with the present invention, the product of the polymerization is isolated by concentrating the polymerization medium, in particular water, by a method such as: distillation, screw extrusion, thin film evaporation, drum evaporation, by means of a belt dryer, or spray drying.

C. Synthesis of Copoly(Succinimide-Aspartate) in a Supercritical Fluid

In another embodiment of the present invention a copoly(succinimide-aspartate) is synthesized in a supercritical fluid at high molecular weight and high yield. In accordance with this embodiment, a mixture of sodium aspartate and ammonium aspartate is prepared in a similar manner to that discussed in the thermal synthesis of copoly(succinimide-aspartate) above. This mixture is then subjected to polymerization in a supercritical fluid in a method similar to that described for the synthesis of polysuccinimide above. The weight average molecular weight is in the order of about 2,000 to about 10,000 Dalton, including all increments within that range, and preferably in the order of from 3,000 to 5,000 Daltons.

In another embodiment of the present invention, the polymerization is carried out in the presence of a thermal stabilizer or an antioxidant or a mixture thereof.

D. Ring-Opening of Polysuccinimide to Form Derivatives

The term "ring-opening" as used in this application denotes the formation of a derivative of polysuccinimide by opening at least one succinimide ring, as shown schematically by the following reaction:

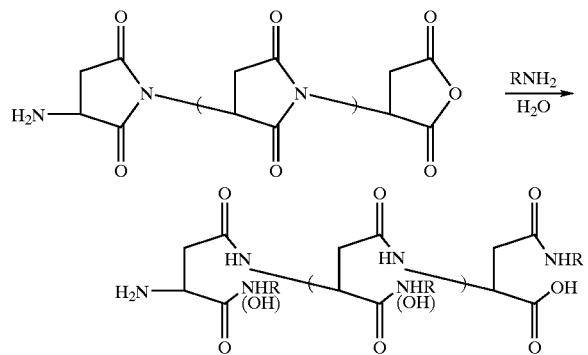

Until now derivatives such as those made from copoly (succinimide-aspartate) have been very difficult to make. We have discovered that polysuccinimide can be derivatized by using combinations of amines. For example, a combination of ammonium hydroxide and 2-aminoethanol resulted in the formation of a resin with free carboxylic acid salts, and the amides of ammonia and aminoethanol. Additional compounds in accordance with the present invention include aminopyridine and imidazole.

It is sometimes preferable to have the polysuccinimide substantially in the absence of sodium salts. The usual salts derived from polysuccinimide hydrolysis with sodium hydroxide result in the sodium polyaspartate. Thus, in another aspect of this invention the succinimide rings are hydrolyzed by a tertiary amine to form the tertiary amine salt of polyaspartic acid.

An amine in accordance with the present invention is any amine of the general formula:

$$R_1R_2R_3N$$

where $R_1$, $R_2$, and $R_3$ are the same or different radicals selected from a hydrogen, an alkyl, such as methyl, ethyl, n-propyl, isopropyl, n-butyl, isobutyl, sec-butyl, t-butyl, n-amyl, isoamyl, t-amyl, n-hexyl, n-octyl, capril, n-decyl, lauryl, myristyl, cetyl, and stearyl; substituted alkyl, such as hydroxyethyl; alkenyl, such as allyl; aryl, such as phenyl; aryl-alkyl, such as benzyl; or substitute aryl radical, such as alkylphenyl, chlorophenyl and nitrophenyl.

Further, a polyamine, such as a diamine, a triamine, a protein, a peptide, a gelatin, chitin, lysine, omithine, or a melamine, can be used to provide additional sites for further reactions. An example of the latter is to open the succinimide ring with an aminoalcohol, such as a diethanolamine, to provide a polyfunctional OH group-containing resin to further react. A further example is to open all the succinimide rings with sufficient diamine, such as hexamethylene diamine, so that no crosslinking can occur but that each amide formed has an amine group at the end. Thus, chemistry can be performed on that amine group, such as a reaction with a polyfunctional isocyanate to chain extend the imide-containing polyamino acid or to form a crosslinked gel. An aminoethoxylate can be used to form a polymer with a long chain ethoxylate. Also, an aminoethoxylate containing a hydrophobic end group can be used to form a rheology modifier or an associative thickener. An additional amino functional material can be used to react in a nucleophilic addition with the imide-containing polyamino acid such as: an allyl. Further, amino polybutadiene and an amino terminated fatty olefin can be used in a nucleophilic addition with the imide-containing polyamino acid which could achieve the same result as an allyl amine and in addition be able to crosslink by an oxidative cure mechanism. Further, an amino-aromatic compound, such as aniline or a substituted aniline can be used in the nucleophilic addition in accordance with the present invention. Preferably, the amine is tertiary amine, more preferably, triethanol amine.

Therefore by the proper combination of various amines, derivatives can be made from polysuccinimide which are similar in functionality to those made from copoly (succinimide-aspartate) but exhibit higher molecular weight and reduced color.

The ring-opening reactions in accordance with the present invention can be carried out either in a supercritical fluid (SCF) or in water.

In another embodiment of the present invention, the polymerization is carried out in the presence of a thermal stabilizer or an antioxidant or a mixture thereof as discussed below.

E. Polymer Additives

The polymers of the present invention may be mixed with a number of additives during the polymerization, prior to isolation, as described above, or post isolation. The additives are selected to impart the desired properties to the end product and to facilitate its fabrication. In the post isolation mixing (compounding) of additives, it is preferred that the polymers, copolymers or derivatives of the present invention are blended with a material to reduce the melt viscosity of the polymers, copolymers or derivatives of the present invention. Such materials include, but are not limited to, a plasticizer or a polymer, other than the polymers in accordance with the present invention, to form a polymer blend; preferably the resulting polymer blend is substantially a miscible polymer blend. Arriving at a specific complex formulation may be the result of an engineering art and experimentation. Preferred polymer additives include, but are not limited to the following:

Stabilizers: During processing a polymer must be brought to the molten state at temperatures much above those of their melting or glass transition. This is done to lower their viscosity and to extend the upper limit of possible processing rates without melt fracture. Consequently there is the real danger of thermal degradation during processing. For this reason heat stabilizers, such as free radical scavengers, maybe used. Polymer chains maybe also sensitive to forms of energy other than thermal. In particular, uses that are intended for outdoor applications must be able to withstand ultraviolet (UV) radiation, for which purpose UV stabilizers are added. In addition the polymer maybe stabilized against oxidative degradation, both short term at elevated processing temperatures, and long term during storage and use. In an oxidative degradation oxygen is absorbed and produces free radicals that react with the chains, usually autocatalytically, and degrade them. Most of the antioxidants combine with the oxygen-generated free radicals and inactivate them.

Antioxidants: Antioxidants are chemical compounds which are incorporated at low concentrations into polymer systems to retard or inhibit polymer oxidation and its resulting degradative effects by atmospheric oxygen. Their use is essential in order to protect the polymer during production, processing, compounding, and end use. Oxidation is a common natural phenomenon which can occur at any phase of a polymer's existence: during polymerization, processing, or end use of the product. The process may cause a variety of chemical and physical changes such as discoloration, loss of gloss or transparency, surface chalking and cracks. Oxidation tends to lower the physical properties of a polymer, such as impact strength, elongation, and tensile strength. The process may continue to degrade a polymer article until it loses its utility. The rate and effects of oxidation differ depending on the polymer, manufacturing process, and morphology.

Auto-oxidation: Organic materials react with molecular oxygen in a process called "auto-oxidation". Auto-oxidation is a free-radical chain reaction and, therefore, can be inhibited at the initiation and propagation steps. The process is initiated when free alkyl radicals (R·) are generated in the polymer by heat, radiation, stress, or residues. Without the protection afforded by antioxidants, these radicals begin a chain reaction which degrades the polymer.

Although Applicants do not wish to be bound to any particular theory, it is generally believed that polymeric oxidation begins when a free radical containing a highly reactive electron reacts with oxygen forming peroxy radicals (ROO·). These react with the polymer to produce hydroperoxides (ROOH) which decompose further to form two new free radicals. These begin the cycle anew, propagating a cascade of reactions that, sometimes in the absence of an antioxidant, can turn into a chain reaction leading to the failure of the polymer. Antioxidants terminate this sequence and eliminate free radicals from the system. Stabilization is achieved either by termination reactions or by inhibiting the formation of free radicals. Primary antioxidants increase the number of terminations while secondary antioxidants reduce the formation of free radicals. Primary and secondary antioxidants are often used together with synergistic results.

Primary antioxidants: Primary antioxidants such as hindered phenols and secondary arylamides interrupt free radical processes by donating labile hydrogen atoms to change propagating hydroperoxy radicals into stable species.

Hindered phenols: Hindered phenols interrupt the auto-oxidation cycle. The hindered phenol is capable of donating hydrogen atoms, undergoing rearrangement reactions, and further reacting with free radicals until it is fully consumed. Over-oxidation of the hindered phenol is undesirable since it causes discoloration. Several approaches to stabilization which avoid over-oxidation of the phenolic have been developed. Trivalent phosphorous compounds and antacids (calcium stearate and zinc stearate) to scavenge acidic catalyst residues are typically used as co-additives in combination with the phenolic. Most of the newer commercial antioxidants are of this type, such as alkylated hydroquinones and phenols. In high temperature applications, polynuclear phenols generally are preferred over monophenols because of their lower sublimation rates. Phenolic antioxidants are typically used at levels ranging from 0.05 to 2.0 wt %.

Amines: The ability of amines, preferably aromatic amines, to stabilize at high temperature makes them useful in applications requiring prolonged exposure to elevated temperatures. Amines can be classified further as ketone-amine condensation products, diaryldiamines, diarylamines, and ketone-diarylamine condensation products. Both solid and liquid products are marketed. Typical use levels are 0.5 to 3%.

Secondary antioxidants: Secondary antioxidants, such as phosphites or thioesters, are peroxide decomposers that undergo redox reactions with hydroperoxides to form stable products. They are cost effective because they can be substituted for a portion of the more costly primary antioxidant and provide equivalent performance.

Phosphites: Phosphites generally are used in combination with other antioxidants, particularly phenols, the most commonly used secondary antioxidants, reduce hydroperoxides to alcohols. Phosphites are highly effective process stabilizers, nondiscoloring, and have broad FDA regulation for many indirect food contact applications. Tri (mixed nonyl- and dinonylphenyl) phosphite is used in the largest volume. Use levels vary from 0.05 to 3.0 wt %.

Thioesters: Thioesters reduce hydroperoxides to alcohols. Thioesters are nondiscoloring, FDA regulated, and incorporated to improve long-term heat stability. Typical use levels are from 0.1 to 0.3 wt % in polyolefins with higher levels used in polymers containing unsaturation.

Synergy between primary and secondary antioxidants: Combinations of certain antioxidants sometimes provide synergistic protection. The most common synergistic combinations are mixtures of antioxidants operating by different mechanisms. For example, combinations of peroxide decomposers may be used with propagation inhibitors. Similarly, combinations of metal chelating agents maybe used with propagation inhibitors. Synergistic combinations of structurally similar antioxidants are also known, particularly combinations of phenols.

Blends of a phenolic and a phosphite are very useful for melt compounding. They work well to maintain the molecular weight of the polymer, while at the same time maintaining low color. The phosphite decomposes hydroperoxides and protects the phenolic during processing thereby preventing (if optimum levels of both are added) over-oxidation of the hindered phenol and inhibiting the formation of colored by-products. This preserves the phenolic for long term thermal stability. Blends of the phenolic antioxidant and a thioester are a good combination for long term thermal stability of the polymer.

Two main classes of antioxidants inhibit the initiation step in thermal auto-oxidation. The peroxide decomposers function by decomposing hydroperoxides through polar reactions. Metal deactivators are strong metal-ion complexing agents that inhibit catalyzed initiation through reduction and oxidation of hydroperoxides. The most important commercial propagation inhibitors are hindered phenols and secondary alkylaryl- and diarylamines.

Additional Antioxidants Include:

Sulfides: Dilauryl thiodipropionate and distearyl thiodipropionate are the most important commercial antioxidants in this class. They are used with phenols to give synergistic combinations.

Metal salts of dithioacids: These substances act as hydroperoxide decomposers and propagation inhibitors, and are used in conjunction with other antioxidants, particularly phenols.

Bound antioxidants: Recently, antioxidants have been developed that are copolymerized into the polymer chain. The main advantage of such a system is low antioxidant extractability in applications where the polymer is in contact with solvents capable of extracting conventional antioxidants.

Additional Additives Include:

Colorants: Preferably, for decorative reasons, colorants such as pigments and dyes that absorb light at specific wavelengths are added to the polymers of the present invention.

Plasticizers: The term "plasticizer" stems from the process of making the polymer more susceptible to plastic flow.

Plasticizers, preferably external plasticizers, are usually monomeric molecules that when mixed with polar or hydrogen bonded polymers, position themselves between these intermolecular bonds and increase the spacing between adjacent bonds. Of course they must also either be polar or be able to form hydrogen bonds. The result of this action is to lower the level of the strength of intermolecular forces, thus decreasing the mechanical strength and increasing the flexibility of the rigid structure. The plasticizer may preferably be introduced to the polymer by copolymerization. In this context copolymerization is sometimes referred to as internal plasticization.

Reinforcing Agents: This category of additives is very broad and yet very important in that such additives improve the mechanical properties of the base polymers, chiefly their strength and stiffness. Short and long glass fibers, graphite fiber are common additives in applications calling for improved mechanical properties, including the absence of creep (dimensional stability). Solid reinforcing agents also extend the upper temperature limit of the use of the base polymer.

Fillers: The main function of fillers is to reduce the cost of the end product. A very inexpensive filler, occupying a fraction of the volume of a plastic article, will have such an economic benefit. Nevertheless, fillers are also often specialty additives; they may be present to reduce the thermal expansion coefficient of the base polymer, to improve its dielectric properties, or to "soften" the polymers (e.g., calcium carbonate).

Lubricants: Lubricants are very low concentration additives that are mixed with polymers to facilitate their flow behavior during processing. There are two categories of lubricant, external and internal. External lubricants are incompatible at all temperatures with the polymer they are used with; therefore during processing they migrate to the melt-metal interface, promoting some effective slippage of the melt by reducing interfacial layer viscosity. Internal lubricants, on the other hand, are polymer compatible at processing temperatures, but incompatible at the use temperature. Therefore, during processing they reduce chain-to-chain intermolecular forces, thus melt viscosity. As the processed plastic products cool, they become incompatible (phase separation) and can eventually migrate to the surface; thus product properties are not permanently affected.

In an additional embodiment in accordance with the present invention, the polysuccinimide, a copolymer or a derivative thereof is processed in a processing equipment. The processing of polymers is discussed extensively in *Principles of Polymer Processing* by R. T. Fenner, Chemical publishing (1979) and *Principles of polymer Processing*, by Z. Tadmor et al, John Wiley & Sons, New York, (1979) both of which are incorporated herein by reference. Following are some aspect concerning the processing of the materials of the present invention:

F. Processing

The materials of the present invention can be further processed by one of the principal methods used to process thermoplastic materials into finished or semifinished products, namely, screw extrusion, injection molding, blow molding and calendering. An important distinction exists between extrusion and calendering on the one hand, and molding techniques on the other, in that while the former are continuous processes, the latter are discontinuous. The term "materials of the present invention" is used to denote polysuccinimide, copoly(succinimide-aspartate), a derivative thereof and a blend thereof with an additive.

Screw Extrusion: In an embodiment in accordance with the present invention the materials of the present invention are extruded. The extrusion process is used to shape a molten polymeric material into a desired form by forcing it through a die. A variety of profiles can be formed in a continuous extrusion which include, but are not limited to, filaments, films and sheets. The required pressure is generated by at least one rotating screw in a heated barrel as shown in FIG. 1. While the form of the die determines the initial shape of the extrudate, its dimensions may be further modified, for example, by stretching, before final cooling and solidification takes place. A screw extruder may also be used, in accordance with the present invention, to further react the polyimide of the present invention by means of introducing a reactant in the extruder through an injection port as shown in the Figure. The segments of the extruder can be separately heated to different temperatures. Further, the position of the injection port can be moved to a different location along the screw of the extruder to facilitate different residence time and reaction time of the reactant within the extruder. It is also possible to add additional injection ports to facilitate the addition of different reactants that require different residence time in the extruder in order to facilitate to desired reaction.

Single-screw Extrusion: The Figure shows the diagrammatic cross-section of a typical single-screw extruder, which is used to melt and to pump the polymer. Solid material in the form of either granules or powder is usually gravity fed through the hopper, although crammer-feeding devices are sometimes used to increase feed rates. The channel is relatively deep in the feed section, the main functions of which are to convey and compound the solids. Melting occurs as a result of the supply of heat from the barrel and mechanical work from the rotation of the screw.

The screw is held in position by an axial thrust bearing and driven by an electric motor via a reduction gearbox. Screw speeds are generally within the range of from 50 to 150 revolutions/minute, and it is usually possible to vary the speed of a particular machine over at least part of this range.

Barrel and die temperatures are maintained by externally mounted heaters, typically of the electrical-resistance type. Individual heaters or groups of heaters are controlled independently via thermocouples sensing the metal temperatures, and different zones of the barrel and die are often controlled at different temperatures. The region of the barrel around the feed pocket is usually water cooled to prevent fusion of the polymer feedstock before it enters the screw channels. Cooling may also be applied to part or all of the screw by passing water or other coolant through a passage at its center, access being via a rotary union on the driven end of the screw.

The size of an extruder is defined by the nominal internal diameter of the barrel. Sizes range from about 25 mm for a laboratory machine, through 60–150 mm for most commercial product extrusions, up to 300 mm or more for homogenization during polymer manufacture. Common thermoplastic extruders have screw length-to-diameter ratios of the order of 25 or more. An important characteristic of a screw is its compression ratio, one definition for which is the ratio between channel depths in the feed and metering sections. This ratio normally lies in the range of from 2 to 4, according to the type of material processed. Output rates obtainable from an extruder vary from about 10 kg/h for the smallest up to 5000 kg/h or more for the largest homogenizers. Screw-drive power requirements are usually of the order of 0.1–0.2 kW h/kg.

Many modifications to the basic form of screw design can be used, often with the aim of improving mixing. Another variant is the two-stage screw, which is effectively two screws in series. The vent of the melt at the end of the first stage, where the screw channel suddenly deepens, makes it possible to extract through a vent any air or volatiles trapped in the polymer.

Multiscrew Extrusion: In addition to single screw extruders, there are twin and multiscrew extruders performing substantially the same functions, twin-screw machines being the most common. Such extruders can have two screws intermeshing or not quite intermeshing, corotating or counter rotating. The more common intermeshing type have distinct advantages over single-screw machines in terms of an improved mixing action, and are not so much screw viscosity pumps as positive displacement pumps.

Extrusion Dies: The simplest extrusion dies are those used to make axisymmetric products such as lace and rod. The main design consideration with such dies is that changes in flow channel diameter from that of the extruder barrel bore to that of the die exit are gradual. Smooth melt flow is thus ensured, with no regions where material can be retained and degraded. In designing dies for more complicated profiles, due allowance must also be made for elastic recovery, which may cause changes in shape after the extrudates leave the dies. Other types of extrusion die are used in the production of flat film, sheet, pipe and tubular film, and in covering wire and cable.

Flat-film and Sheet Extrusion: The distinction between flat film and sheet is one of thickness, both being extruded in similar types of dies. As the widths of such flat sections are much greater than the extruder-barrel diameters, the dies must spread the melt flow laterally and produce extrudates of as uniform a thickness as possible.

Pipe, Tube and Profile Extrusion: Pipe, tube and profile extrusion process is another extrusion operation. Pipes and tubes are usually distinguished by size. Below 1.25 cm (0.5 in) diameter is called a tube; above 1.25 cm (0.5 in) diameter is called a pipe.

Wire and Cable Covering: Wire and cable covering operations are carried out over a very wide range of line speeds, from about 1 m/min for large high-voltage electrical cables to 1000 m/min or more for small-diameter wires. Nevertheless, the types of die used are similar, being of the crosshead type to accommodate the conductor entering at an angle—often a right angle—to the axis of the extruder. The success of such an arrangement depends on the design of the flow deflector, which serves to distribute the melt into a layer of uniform thickness on the conductor.

Injection Molding: The term "injection molding" as used herein denotes the process for producing substantially identical articles from a hollow mold. In the injection molding process, molten polymer is forced under high pressure into a closed mold of the required shape, where it is cooled before the mold is opened and the finished article extracted.

Blow Molding: Blow molding is used for the formation of hollow articles, such as bottles and other containers, manufactured by the blow molding process. The blow molding process involves first the formation of a molten parison, which is a preshaped sleeve, usually made by extrusion. Air is blown into the parison surrounded between two mold halves expending the parison and causing it to take the shape of the mold. The polymer solidifies and the hollow article is ejected.

Calendering: The term "calendering" as used herein denotes a process for producing continuous films or sheets by pressing molten polymer between rotating rolls.

Another process that is very important for the production of fibers and filaments is that of spinning. Melt supplied by either an extruder or gear pump is forced vertically downwards through a series of very small holes in a flat plate or spinneret, and the resulting threads are air cooled and rapidly stretched by winding at high speed on to a bobbin.

Further, the polymers and copolymer of the present invention can be worked by engineering techniques including welding, cutting and machining, although to do so to any significant extent is to lose the advantage offered by polymeric materials over metals in terms of ease of fabrication.

Having generally described this invention, a further understanding can be obtained by reference to certain specific examples which are provided herein for purposes of illustration only and are not intended to be limiting unless otherwise specified.

EXAMPLES

1. The Triethanolamine Salt of Polyaspartic Acid from Polysuccinimide (PSI)

To 5 grams (51.5 mEq of succinimide residues) of Polysuccinimide (MW=34,500 Daltons) was added 7.74 grams (51.9 mEq) of Triethanolamine and 23.34 grams of double distilled water. This dispersion was placed into an oven at 80° C. with a magnetic stirrer for 29 hours. The solution was reddish and had some residual solids which were filtered out (note: this sample of PSI when hydrolyzed with NaOH also has residual solids).

TABLE 1

Results of the Titration Filtrate

| Species | Measured (mEq/g solids) | Theoretical (mEq/g solids) |
|---------|------------------------|----------------------------|
| COOH    | 3.34                   | 3.73                       |
| Amine   | 4.95                   | 3.76                       |

Therefore the degree of hydrolysis is 89.5% with remaining excess of 31.6% amine.

Figure 2:
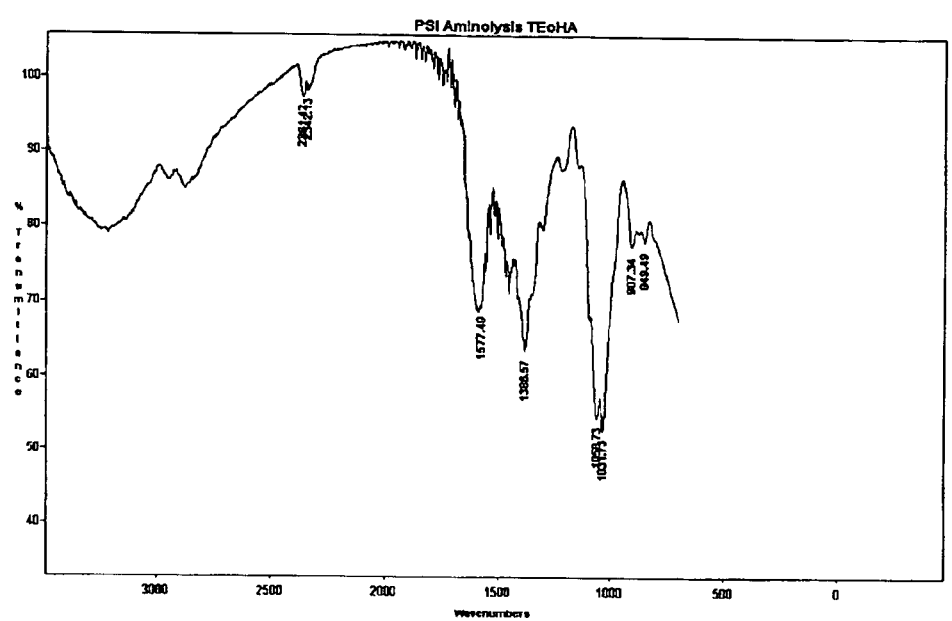
FIG. 2 is an FTIR spectrum of a sample treated with excess triethanolamine. As seen in the spectrum there is no peak at 1710 wave numbers where the succinimide ring absorbs. The peak at 1577 is for the amide backbone, while the peak at 1386 is for the carboxylate group. The strong peaks at 1030-1060 are the triethanolamine.

The FTIR spectrum of another sample, treated with excess triethanolamine is shown in FIG. 2. As seen there is no peak at 1710 wave numbers where the succinimide ring absorbs. The peak at 1577 is for the amide backbone, while the peak at 1386 is for the carboxylate group. The strong peaks at 1030-1060 are the triethanolamine.

This was repeated on a larger scale:

41.4 g of PSI (426 mEq of succinimide residues)
65.3 g of triethanolamine (438 mEq of triethanol amine (TEOHA))
65.4 g of water The dispersion was placed into an 80° C. oven, with magnetic stirring, for overnight. The next morning the solution was clear, reddish, and viscous. Total solids (TS) was 66.05%.

TABLE 2

Titration Results

| Species | Measured (mEq/g solids) | Theoretical (mEq/g solids) |
|---------|------------------------|----------------------------|
| COOH    | 3.23                   | 3.73                       |
| Amine   | 4.04                   | 3.83                       |

Therefore the degree of hydrolysis is 86.6% with remaining excess of 5.5% amine.

1. Derivatization of Polysuccinimide (PSI)

Polysuccinimide was treated with a varying relative amounts of ammonia/2-aminoethanol in water. Solutions of ammonia and 2-aminoethanol were prepared and solid PSI added as shown in Table 3:

TABLE 3

Solutions of ammonia and 2-aminoethanol

| Ingredient | 100% Ammonia amount | mEq | 65% Ammonia amount | mEq | 32% Ammonia amount | mEq | 0% Ammonia amount | mEq |
|---|---|---|---|---|---|---|---|---|
| Concentration of Ammonia | 2.94 ml | 51.5 | 1.91 ml | 33.4 | 0.94 ml | 16.5 | 0 ml | 0 |
| 2-aminoethanol | 0 g | 0 | 1.1 g | 18.0 | 2.14 g | 35.1 | 3.14 g | 51.5 |
| Water | 22 ml | | 22 ml | | 22 ml | | 22 ml | |
| PSI | 5 g | 51.5 | 5 g | 51.5 | 5 g | 51.5 | 5 g | 51.5 |

The dispersions were placed into an 80° C. oven, with magnetic stirring for 2 hours. The dispersions changed into bright yellow solutions within 1 hour. Total solids (TS) were determined and the solutions were titrated and presented in Table 4.

TABLE 4

Total solids (TS)

| | 100% Ammonia | 65% Ammonia | 32% Ammonia | 0% Ammonia |
|---|---|---|---|---|
| % TS | 21.170 | 23.860 | 26.056 | 28.132 |
| COOH Titer mEq/g | 4.407 | 4.073 | 3.733 | 3.392 |

The titer expected for an ammonia salt of poly(aspartic acid) is 7.576 mEq/g. The calculated titer for a 50% ammonia salt/50% ammonia amide is 4.065. The calculation for all the mixtures is presented in Table 5.

TABLE 5

Measured and Calculated COOH Group

| Titer mEq/g | 100% Ammonia | 65% Ammonia | 32% Ammonia | 0% Ammonia |
|---|---|---|---|---|
| Measured | 4.407 | 4.073 | 3.733 | 3.392 |
| Calculated | 4.065 | 3.826 | 3.624 | 3.448 |

This demonstrates that derivatization by the amines/ammonia to form amides has taken place but also that water competes with the amines/ammonia for the succinimide ring so that more than 50% of the succinimide rings are hydrolyzed to form the carboxylic acid salt of the amines rather than forming the amides.

Inspection of the FTIR of ethanolamine shows a peak at 1067 wavenumbers. This peak is not in the sample with 100% ammonia and is shown to grow as the ammonia level in the system decreases and the aminoethanol level increases.

2. Additional Derivatization of Polysuccinimide (PSI)

In this example the t-amine, triethanolamine, is used in conjunction with 2-aminoethanol to form a copolymer of aspartate and the triethanolamine aspartate amide.

TABLE 5

Solution of water, 2-aminoethanol and triethanolamine

| Ingredients | Weight (grams) | Total mEq |
|---|---|---|
| Water | 137 | |
| 2-Aminoethanol | 15.7 | 257.7 |
| Triethanolamine | 36.5 | 257.7 |
| Polysuccinimide | 50 | 515.5 of succinimide residues |

The amines are dissolved in the water and the solid polysuccinimide is added, with magnetic stirring, to the solution. The resulting dispersion is placed into an 80° C. oven, with magnetic stirring, overnight.
The product was titrated with the following results:

COOH Titer: 383.0 mEq (therefore there are 132.5 mEq as Amide)
"NH" Titer: 387.9 mEq (since there are 257.7 mEq of t-amine there are 130.2 mEq of 2-aminoethanol remaining).

Thus there are 127.5 mEq of 2-aminoethanol present as the aspartate amide in the copolymer, which is close to the amount calculated from the COOH titer.

Obviously, numerous modifications and variations of the present invention are possible in light of the above teachings. It is therefore to be understood that within the scope of the appended claims, the invention may be practiced otherwise than as specifically described herein.

What is claimed is:

1. A method for preparing a polysuccinimide derivative, which comprises, subjecting the polysuccinimide to a ring-opening reaction; wherein said polysuccinimide is formed by polymerization of L-aspartic acid a supercritical fluid.

2. The method of claim 1, wherein said ring-opening reaction is carried out in a supercritical fluid.

3. The method of claim 1, wherein said ring-opening reaction is carried out subsequently to the formation of polysuccinimide in a supercritical fluid.

4. The method of claim 1, wherein said ring-opening reaction is carried out in water.

5. The method of claim 1, wherein said ring-opening reaction is carried out in the presence of an amine.

6. The method of claim 5, further comprising water as a cosolvent.

7. The method of claim 6, wherein said amine is a combination of amines.

8. The method of claim 7, wherein said combination of amines is comprised of ammonium hydroxide and 2-aminoethanol to form a resin.

9. The method of claim 8, wherein said resin contains a free carboxylic acid salt and the amides of ammonia and aminoethanol.

10. The method of claim 5, wherein said amine has the general formula: $R_1R_2R_3N$; where $R_1$, $R_2$, and $R_3$ are the same or different radicals selected from the group consisting of hydrogen, an alkyl, a substituted alkyl, an alkenyl, an aryl, an aryl-alkyl, and a substituted aryl radical.

11. The method of claim 10, wherein said alkyl is selected from the group consisting of methyl, ethyl, n-propyl, isopropyl, n-butyl, isobutyl, sec-butyl, t-butyl, n-amyl, isoamyl, t-amyl, n-hexyl, n-octyl, capril, n-decyl, lauryl, myristyl, cetyl, and stearyl.

12. The method of claim 10, wherein said substituted alkyl is hydroxyethyl.

13. The method of claim 10, wherein said alkenyl allyl.

14. The method of claim 10, wherein said aryl is phenyl.

15. The method of claim 10, wherein said aryl-alkyl is benzyl.

16. The method of claim 10, wherein said substituted aryl radical is selected from the group consisting of alkylphenyl, chlorophenyl and nitrophenyl.

17. The method of claim 5, wherein said amine is triethanol amine.

18. The method of claim 5, wherein said amine is selected from the group consisting of aminopyrdine, imidazole and a polyamine.

19. The method of claim 18, wherein said polyamine is selected from the group consisting of a gelatin, chitin, lysine, ornithine and melamine.

20. The method of claim 5, wherein said amine is aminoethoxylate.

21. A derivative formed by the method of claim 1.

22. The method of claim 1, wherein said polymerization is carried out in the presence of a stabilizer.

23. The method of claim 22, wherein said stabilizer is selected from the group consisting of a thermal stabilizer, an antioxidant and a mixture thereof.

* * * * *

UNITED STATES PATENT AND TRADEMARK OFFICE
CERTIFICATE OF CORRECTION

PATENT NO. : 6,903,181 B2
DATED : June 7, 2005
INVENTOR(S) : Swift et al.

It is certified that error appears in the above-identified patent and that said Letters Patent is hereby corrected as shown below:

Column 9,
Line 59, "omithine" should read -- ornithine --.

Column 18,
Line 52, "acid a supercritical fluid" should read -- acid in a supercritical fluid --.

Column 19,
Line 16, "alkenyl allyl" should read -- alkenyl is allyl --.

Signed and Sealed this

Sixth Day of September, 2005

JON W. DUDAS
*Director of the United States Patent and Trademark Office*